United States Patent [19]

Kravitz

[11] Patent Number: 4,976,615
[45] Date of Patent: Dec. 11, 1990

[54] ENDODONTIC DEVICE

[76] Inventor: Leslie Kravitz, 206 Forest Ct., Carboro, N.C. 27510

[21] Appl. No.: 417,592

[22] Filed: Oct. 5, 1989

[51] Int. Cl.$^5$ .............................................. A61C 3/00
[52] U.S. Cl. ....................................... 433/75; 433/102
[58] Field of Search ................... 433/72, 75, 102, 25, 433/165, 229; 33/513, 514

[56] References Cited

U.S. PATENT DOCUMENTS

| | | | |
|---|---|---|---|
| 3,964,170 | 6/1976 | Zdarsky | 433/72 |
| 4,028,810 | 6/1977 | Vice | 433/75 |
| 4,252,522 | 2/1981 | Petty et al. | 433/75 |
| 4,462,802 | 7/1984 | Sekiya | 433/72 |
| 4,708,651 | 11/1987 | Buchanan | 433/72 |

FOREIGN PATENT DOCUMENTS

| | | | |
|---|---|---|---|
| 3431598 | 3/1986 | Fed. Rep. of Germany | 433/25 |
| 3434786 | 4/1986 | Fed. Rep. of Germany | 433/72 |

*Primary Examiner*—Gene Mancene
*Assistant Examiner*—Michael Lynch
*Attorney, Agent, or Firm*—McAulay Fisher Nissen & Goldberg

[57] ABSTRACT

An endodontic device in the form of a platform adapted to be mounted on a dentist's finger. A foam insert holder mounted on the platform is adapted to receive a removable foam insert for holding a plurality of root canal instruments. An open-ended slot formed in the platform is adapted to receive one of the instruments. Scale indicia is provided on the platform adjacent to the slot to permit adjustment of the working length of the instrument in the slot to guide the dentist in using the instrument during a root canal procedure. The platform also is formed having a plurality of instrument receiving holes to permit curving of the instrument where desired. The platform further has a plurality of finger-operated indexing plates having indicia to permit the dentist to assign a separate indication of the working length in each root canal being worked on.

14 Claims, 3 Drawing Sheets

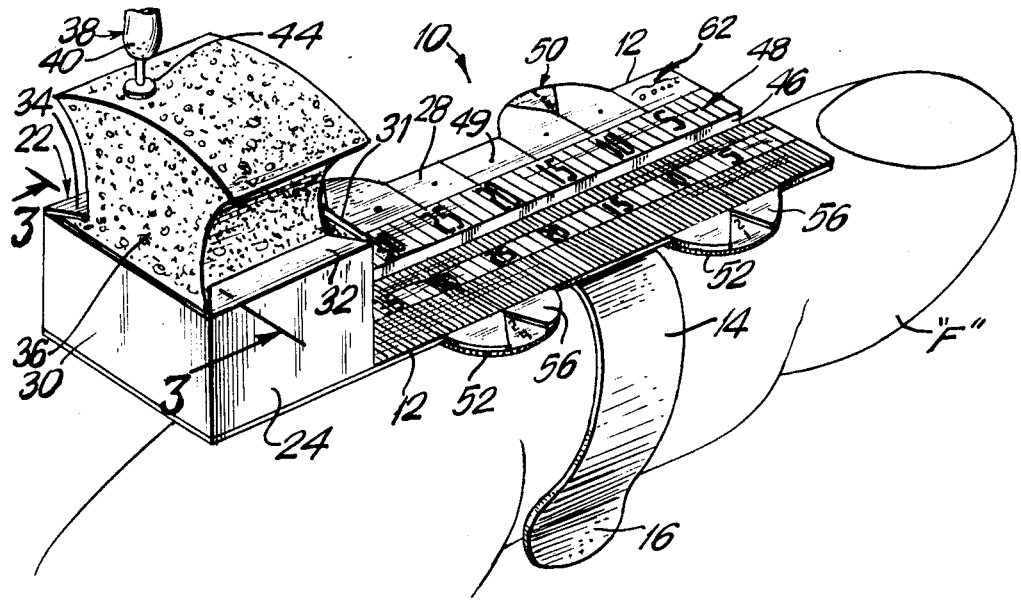
FIG. 2
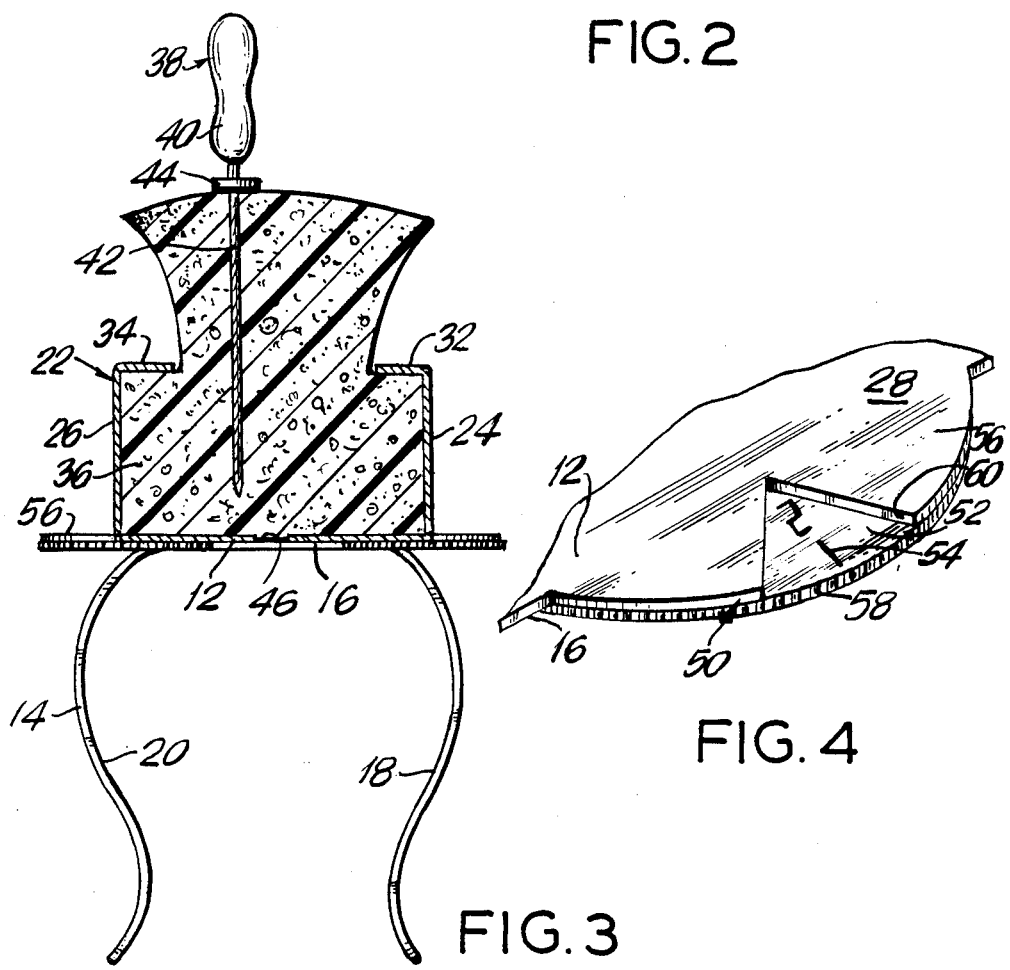
FIG. 3
FIG. 4

ENDODONTIC DEVICE

BACKGROUND OF THE INVENTION

I. Field of the Invention

This invention relates generally to an endodontic device and, more particularly, to a device intended to be mounted on the dentist's finger to permit the endodontic procedure to be performed more quickly and efficiently.

II. Description of the Prior Art

In the course of performing dental work, when it is found that a tooth requires a conventional endodontic procedure, it generally is necessary for the dentist to perform nonsurgical root canal therapy on the tooth. Typically, the dentist ascertains the depth through which the various size root canal instruments should penetrate into the root canal for removing the pulpal tissues from the root canal system. To assist the dentist in his or her work, there are know measuring devices wherein the root canal instruments are equipped with stoppers located at the proper point along each root canal instrument intended to be used, to ensure that the latter is inserted the proper depth into the root canal. These stoppers, which are typically formed of rubber or plastic, set the root canal instrument to the proper length or penetration depth for the root canal. This is normally determined by taking a radiograph of the tooth to be treated. During the root canal therapy, different size root canal instruments are usually employed as the work progresses.

Typical of such known measuring or gauging devices are U.S. Pat. No. 3,964,170 issued to Eduard Zdarsky on June 22, 1976, and U.S. Pat. No. 4,212,639 issued to Alfred Schaffner on July 15, 1980. While the gauges of these patents permit the dentist to accurately set the correct length or depth of penetration of root canal instruments, the use thereof is time consuming. This can introduce unnecessary delays in the endodontic procedure; particularly where it is important that the therapy be carried out with maximum speed and efficiency.

It also is known to have a finger mounted platform intended to be worn by the dentist, and having scale indicia thereon to permit the dentist to adjust the working length of the instrument. Generally, this is done by positioning the instrument on top of the scale. However, it is difficult to make an accurate adjustment since the instrument has a tendency to slide or move-about the scale during the adjustment procedure.

Still, further, it is known to provide a slot or groove in a plate, together with scale indicia on the plate alongside the slot. The plate is a separate member not intended to be worn or mounted on the dentist's finger. In use, the slot receives the instrument and, thus, reduces the tendency of the instrument to move about unnecessarily during the adjustment.

To the extent these heretofore known devices provide a useful function, they are limited in that they permit the dentist to perform only one function; namely, adjusting the working length of the instrument. The dentist still must reach away from the patient, and away from the field of operation, to select another instrument, when necessary, to perform a particular sequence in the procedure.

Also, there are times when the dentist may wish to curve the instrument depending on the curvature of the root being worked on. The present known devices do not combine these adjusting features in the same gauge.

Still, further, since the dentist typically is working on more than one root canal of the same tooth during the same procedure, the dentist has to either write down the working length of each root canal on a chart, or commit the different lengths to memory. Referring repeatedly to the separate lengths in the patient's record introduces further unwanted delay in the endodontic procedure while committing the different lengths to memory introduces the possibility of error in attributing an incorrect length to the root canal being worked on.

The present invention simplifies the endodontic procedure by providing a finger mounted platform having multiple features which enable the dentist to quickly perform a plurality of functions during the procedure in the manner hereinafter described.

SUMMARY OF THE INVENTION

The endodontic device of the present invention provides for an elongated platform having a ring-like shank for mounting the platform on the dentist's finger. Mounted on one end of the platform is a foam insert holder adapted to retain a removable foam insert for holding and storing a plurality of differently sized root canal instruments. An open-ended slot extends longitudinally along the length of the platform and is adapted to receive one of said root canal instruments. The open end of the slot is located at the other end of the platform opposite to where the foam insert holder is mounted. Scale indicia is provided on the platform located adjacent to the slot to permit adjustment of the working length of the instrument in the slot thereby to guide the dentist in using the instrument in the course of performing a root canal procedure on a patient's tooth.

The platform further is provided with a plurality of instrument receiving holes, each having a pre-determined diameter adapted to permit insertion of a substantially correspondingly sized root canal instrument for curving the instrument where desired.

There further is provided a plurality of finger-operated indexing assemblies in the form of a plate rotatably mounted to the bottom surface of the platform. The plate has numerical indicia thereon which is selectively exposed to view through an opening in the platform. In use, the plate is rotatable by the dentist to a dialed position to permit selected indicia to be seen through the opening in the platform, which indicia corresponds to the working length of the root canal being worked on.

Additional features and advantages of the present invention will become apparent from a consideration of the following detailed description when taken in conjunction with the accompanying drawings.

BRIEF DESCRIPTION OF THE DRAWINGS

FIG. 2 is a perspective view of the endodontic device of FIG. 1 mounted on a finger, and further showing a plurality of root canal instruments inserted in a foam insert adapted to be mounted on the device;

FIG. 3 is a sectional view taken along line 3—3 of FIG. 2;

FIG. 4 is an enlarged fragmented view, in perspective, of one of the finger-operated indexing assemblies of the device.

DESCRIPTION OF THE PREFERRED EMBODIMENT

Figure 1:
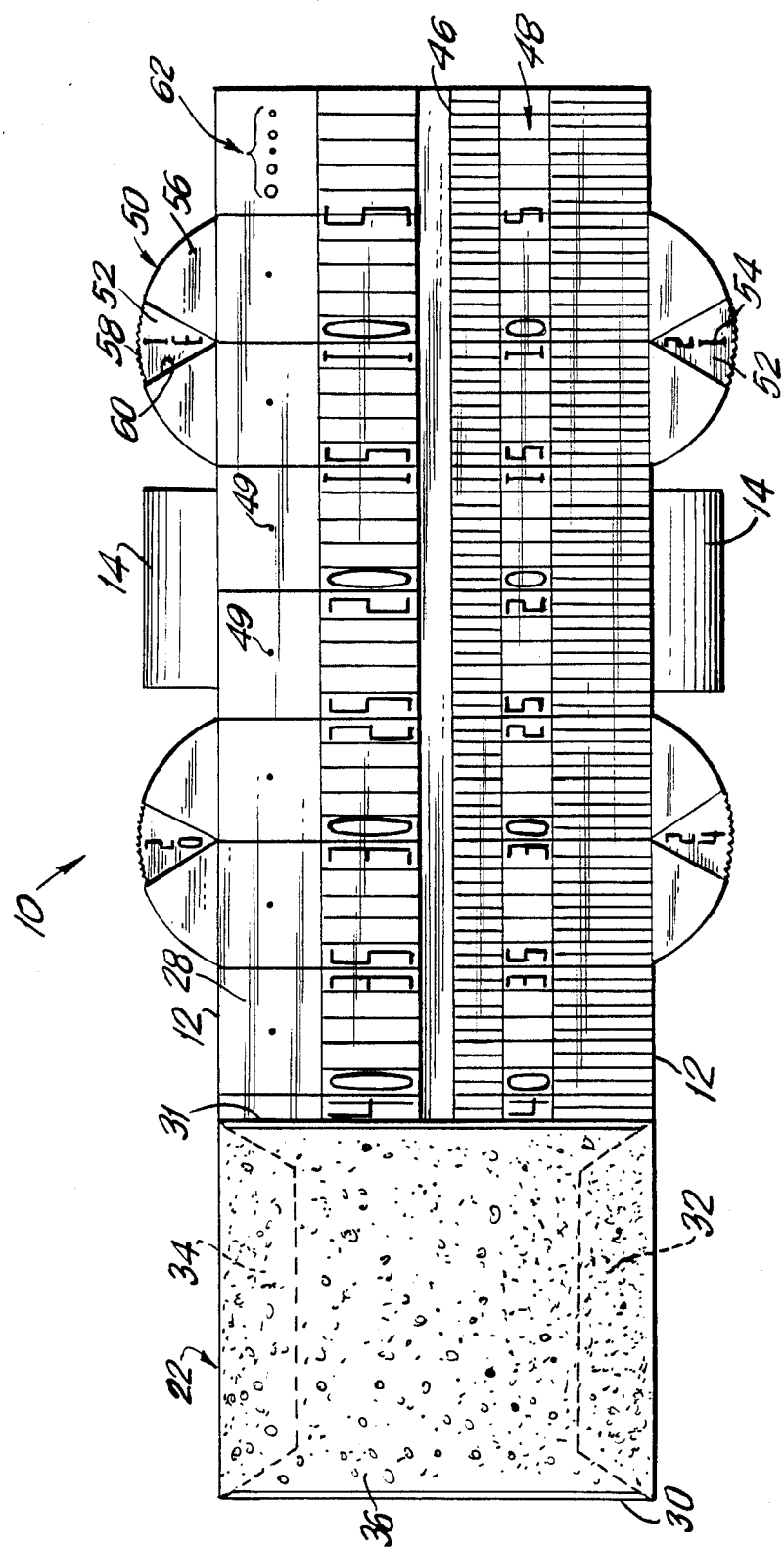
FIG. 1 is a top plan view of the endodontic device constructed in accordance with the present invention.

Referring to the drawings, numeral 10 represents an endodontic device constructed in accordance with the present invention. Device 10 comprises an elongated plate 12 which defines a platform having a length greater than its width. Plate 12 is preferably made of stainless steel, for ease in sterilization, having approximate rectangular dimensions of 56 mm in length, 17.50 mm in width, and between 1.50 and 3.0 mm in thickness. These dimensions, as well as others hereinafter described, are purely illustrative and are not to be deemed limitations on the invention.

A ring-like shank 14 is provided intermediate the longitudinal ends of plate 12 to facilitate mounting the plate on the finger "F" of a dentist, as shown in FIG. 2. The shank 14 may be suitably riveted or welded to the bottom surface 16 of plate 12 in a conventional manner. The shank 14 is open-ended, as shown in FIG. 3, for ease in mounting on the finger, with the opposed segments 18 and 20 movably adjustable relative to each other to accommodate differently sized fingers. Shank 14 is made of the same material as plate 12. Shank 14 is formed having an approximate width of 8.0 mm and an approximate thickness of 0.50 mm. The height of shank 14, as viewed in FIG. 3, measured downwardly on a line perpendicular to the bottom surface 16 of plate 12, is approximately 27.0 mm.

Mounted on one end of plate or platform 12 is a foam insert holder represented generally by numeral 22. Foam insert holder 22 is formed having opposed side walls 24 and 26 and opposed end walls 30 and 31 suitably connected to platform 12, and which walls project upwardly from the platform. The holder may include a base wall (not shown) suitably mounted to the top surface 28 of platform 12. The upper portions of side walls 24 and 26 are tapered and turned inwardly toward each other thereby defining spaced-apart flanges 32 and 34, respectively. The top portion of holder 22 is open to receive a removable foam insert 36 for holding and storing a plurality of differently sized root canal instruments represented generally by numeral 38. The wall thickness of holder 22 is approximately 0.50 mm. The length of walls 24 and 26 is approximately 15.0 mm and the length of end walls 30 and 31 corresponds to the width of platform 12 which is approximately 17.5 mm. The height of walls 24, 26, 30 and 31 is approximately 12.0 mm and the width of flange portions 32 and 34 is approximately 4.0 mm. The material of foam insert holder 22 corresponds to that of platform 12.

As is customary, instruments 38 each have a handle gripping portion 40 and a working portion 42. A rubber or plastic stopper 44 is capable of being adjustably positioned along the length of the instrument to adjust the working length of the instrument in the manner hereinafter described.

Figure 5:
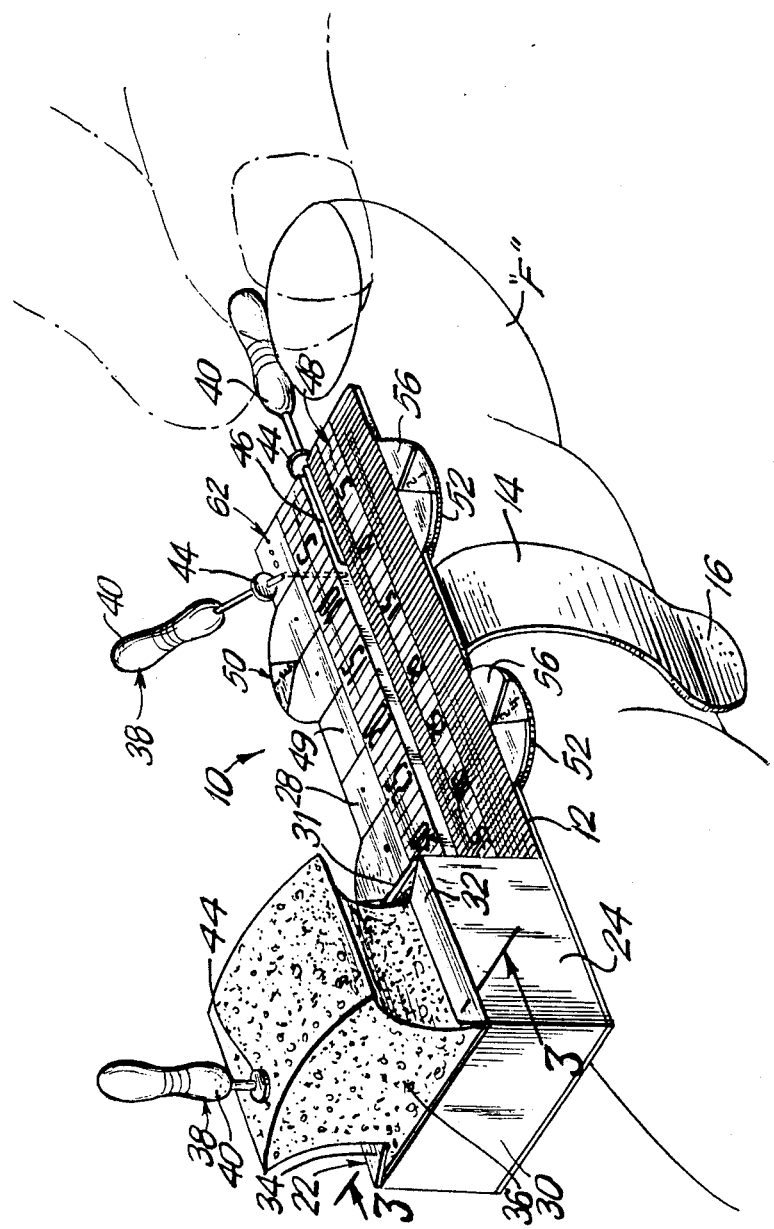
FIG. 5 is a view similar to FIG. 2 showing the device in use for adjusting the working length of an instrument, and for curving an instrument where desired.

An open-ended slot 46 is formed in the top surface 28 of platform 12 which extends longitudinally along the length of the platform. The open end of slot 46 is located at the end of platform 12 opposite to the end which supports foam insert holder 22. The slot 46 is located approximately midway the width of platform 12 and extends substantially parallel to the longitudinally extending sides of the platform. The central slot 46 has an approximate width of 1.5 mm and an approximate depth of 1.0 mm. The slot is suitably sized to receive the working portion 42 of instrument 38 as shown in FIG. 5.

Scale indicia, represented generally by numeral 48, is provided on the top surface 28 of platform 12, located adjacent to slot 46. The indicia 48 includes line markings in 0.50 mm lengths along one side of slot 46 and 1.0 mm lengths along the other side of the slot. Cumulative numerical markings also are provided every 5 mm along the length of the platform. Additional markings, represented by numeral 49, serve to divide each of the cumulative 5 mm distances in half. Accordingly, it will now become apparent that the dentist can insert an instrument 38 into the open end of slot 46 to a length corresponding to the depth of the root canal being worked on. Once the working length of the root canal is determined, the stopper 44 is slid along the instrument and positioned against the end edge of the platform. The working length of the instrument is thus adjusted to insure that the instrument is inserted the proper depth into the root canal system during the endodontic procedure.

It often is the case that the dentist will be working on more than one root canal during an endodontic procedure. Since the working depth of each root canal generally varies from root canal to root canal, it is crucial that the correct working depth be associated with the root canal being worked on. To this end, device 10 provides for a plurality of finger-operated indexing assemblies, represented generally by numeral 50, having indicia thereon to permit the dentist to assign a separate indication of the working length in each root canal being worked on.

Referring to FIGS. 1 and 4, each indexing assembly 50 comprises a circular plate 52 rotatably mounted to the bottom surface 16 of platform 12. Device 10 provides for four such indexing assemblies since the tooth being worked on could have as many as four separate canals. Each plate 52 has numerical indicia or markings 54 representing units of length in the same scale as the units of length represented by scale indicia 48.

The plates 52 are conveniently positioned along the longitudinal edges of platform 12, with two of such plates positioned along each edge. It will be appreciated that the plates could be positioned at other locations on the platform.

In the preferred embodiment, platform 12 has four accurate segments 56 projecting outwardly from the longitudinal edges, and the plates 52 are connected to platform 12 in the region beneath such segments. The peripheral edge of each plate 52 is ridged or knurled, as represented by numeral 58, for ease in manipulating or rotating the plate. A portion of each segment 56 is cut-out to define an opening 60 to expose a portion of the indicia bearing plate 52 therethrough. Accordingly, it will now become apparent that the dentist can rotate a particular plate 52 to a dialed position to permit selected indicia to be exposed to view through plate opening 60, whereby the selected indicia corresponds to the working length of the root canal being worked on. As will be appreciated, a separate indexing assembly is used for each root canal. As such, the working length for each root canal need not be committed to memory or repeatedly referred to in the patient's record.

The diameter of each plate 52 is approximately 10.0 mm and the thickness is approximately 0.50 mm. Also, the markings for scale indicia 48 are preferably in black whereas the plate indicia 54 may be in a contrasting color, such as red.

As will be appreciated, many roots are curved. As a result, dentists typically prefer to use an instrument having a curvature closely approximating the curvature of the root. Since root curvature varies from tooth to tooth, instruments do not come with a pre-set curvature. Instead, the instruments are made straight which is fine for the those roots that are straight. The present invention provides for platform 12 to be constructed having a plurality of instrument receiving holes, represented generally by numeral 62. In the preferred embodiment, there are four of such holes each having a pre-determined diameter. A set of such holes 62 is aligned in a horizontal row in the upper right hand portion of platform 12, as viewed in FIG. 1. If desired, another set of such holes may be formed elsewhere in the device, such as on end wall 31 of foam insert holder 22, which holes may extend lengthwise of the wall adjacent the juncture of said wall with platform 12. Holes 62 are dental round bur size numbers 2, 1, ½, and ¼ which approximately correspond to diameters of 0.9 mm, 0.7 mm, 0.5 mm and 0.25 mm, respectively. The holes pass through the thickness of platform 12. Accordingly, it will now become apparent that the dentist need only insert an instrument of a certain diameter in a selected hole to gradually curve the instrument, as desired, against the edge defining said hole, to a shape corresponding to the curvature of the root canal system being worked on.

It further will be appreciated that all of the features described above may be performed while device 10 is worn on the dentist's finger during the endodontic therapy. This simplifies the endodontic therapy and permits the procedure to be performed more quickly and efficiently than would otherwise be the case without use of the device.

While a preferred embodiment of the invention has been shown and described in detail, it will be readily understood and appreciated that numerous omissions, changes, and additions may be made without departing from the spirit and scope of the invention.

What is claimed is:

1. An endodontic device comprising:
   a platform having a length greater than its width;
   means connected to said platform for mounting said platform on the finger of a dentist;
   said platform having an open-ended slot extending longitudinally along the length thereof, and adapted to receive a root canal instrument;
   scale indicia on said platform and located adjacent to said slot to permit adjustment of the working length of said instrument while in said slot to guide the dentist in using said instrument during endodontic therapy on a patient's tooth; and
   a plurality of finger-operated indexing means along at least one edge of said platform, said indexing means having indicia to permit the dentist to assign a separate indication of the working length in each root canal being worked on.

2. The endodontic device of claim 1 wherein each of said indexing means comprises a plate rotatably mounted to the bottom surface of said platform, said plate having numerical indicia thereon, and said platform having an opening to expose a portion of said indicia bearing plate therethrough, whereby said plate is rotatable by the dentist to a dialed position to permit selected indicia to be exposed to view through said opening, said selected indicia corresponding to the working length of the root canal being worked on.

3. The endodontic device of claim 1 wherein said indicia associated with said indexing means indicates units of length in the same scale as the units of length on said scale adjacent said slot.

4. The endodontic device of claim 1 wherein said indexing means are disposed along a longitudinal edge of said platform.

5. The endodontic device of claim 1 wherein said indexing means are disposed along the opposite longitudinal edges of said platform.

6. The endodontic device of claim 1 wherein said mounting means comprises a ring-like shank connected to said platform.

7. The endodontic device of claim 6 wherein said shank is adjustable to accommodate differently-sized fingers.

8. The endodontic device of claim 1 wherein said platform further has a plurality of instrument receiving holes, each of said holes having a predetermined diameter adapted to permit insertion of a substantially correspondingly sized root canal instrument for curving said instrument against an edge surface of the associated hole.

9. The endodontic device of claim 1 wherein said platform further comprises a foam insert holder adapted to retain a removable foam insert for holding root canal instruments, said holder being at one longitudinal end of said platform and said slot having its open end at the opposite end of said platform.

10. The endodontic device of claim 1 wherein said platform further comprises means for holding root canal instruments.

11. The endodontic device of claim 10 wherein said holding means is located at one longitudinal end of said platform and the open end of the slot is at the opposite end of said platform.

12. The endodontic device of claim 11 wherein said holding means is adapted to secure a removable insert for holding root canal instruments.

13. An endodontic device comprising:
   a platform having a length greater than its width;
   means connected to said platform for mounting said platform on the finger of a dentist;
   a foam insert holder mounted on said platform and adapted to retain a removable foam insert for holding root canal instruments;
   said platform having an open-ended slot extending longitudinally along the length thereof and adapted to receive a root canal instrument, said slot having its open end at one longitudinal end of said platform and said foam insert holder being at the opposite end of said platform;
   scale indicia on said platform and located adjacent to said slot to permit adjustment of the working length of said instrument in said slot to guide the dentist in using said instrument during an endodontic procedure on a patient's tooth;
   said platform further having a plurality of instrument receiving holes, each of said holes having a predetermined diameter adapted to permit insertion of a substantially correspondingly sized root canal instrument for curving said instrument against an edge surface of the associated hole; and
   a plurality of finger-operated indexing means along at least one edge of said platform, said indexing means having indicia to permit the dentist to assign a separate indication of the working length in each root canal being worked on.

14. The endodontic device of claim 13 wherein each of said indexing means comprises a plate rotatably mounted to the bottom surface of said platform, said plate having numerical indicia thereon, and said platform having an opening to expose a portion of said indicia bearing plate therethrough, whereby said plate is rotatable by the dentist to a dialed position to permit selected indicia to be exposed to view through said opening, said selected indicia corresponding to the working length of the root canal being worked on.

* * * * *